(12) United States Patent
Challand et al.

(10) Patent No.: US 8,703,992 B2
(45) Date of Patent: Apr. 22, 2014

(54) METHOD FOR PRODUCING AROMATIC AND HETEROAROMATIC CARBOXYLIC ACIDS, CARBOXYLIC ACID ESTERS AND CARBOXYLIC ACID AMIDES

(75) Inventors: Nina Challand, Mannheim (DE); Ansgar Gereon Altenhoff, Heidelberg (DE); Joachim Schmidt-Leithoff, Mannheim (DE); Kathrin Wissel-Stoll, Ludwigshafen (DE); Michael Rack, Eppelheim (DE); Joachim Rheinheimer, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 384 days.

(21) Appl. No.: 12/994,271

(22) PCT Filed: May 25, 2009

(86) PCT No.: PCT/EP2009/056302
§ 371 (c)(1),
(2), (4) Date: Feb. 11, 2011

(87) PCT Pub. No.: WO2009/144197
PCT Pub. Date: Dec. 3, 2009

(65) Prior Publication Data
US 2011/0172456 A1     Jul. 14, 2011

(30) Foreign Application Priority Data
May 27, 2008 (EP) ...................... 08156993

(51) Int. Cl.
*C07C 67/36* (2006.01)

(52) U.S. Cl.
USPC ................ 560/97; 560/51; 560/103

(58) Field of Classification Search
USPC ............................ 560/103, 51, 97
See application file for complete search history.

(56) References Cited

U.S. PATENT DOCUMENTS

| 5,344,961 | A | 9/1994 | Drent | |
|---|---|---|---|---|
| 6,537,944 | B1 * | 3/2003 | Zoeller et al. | 502/180 |
| 6,653,502 | B2 * | 11/2003 | Geissler | 560/97 |
| 2003/0191339 | A1 * | 10/2003 | Schfer et al. | 560/97 |
| 2004/0068131 | A1 * | 4/2004 | Beller et al. | 556/13 |
| 2008/0039633 | A1 * | 2/2008 | Jung et al. | 546/304 |
| 2010/0174094 | A1 | 7/2010 | Zierke et al. | |

FOREIGN PATENT DOCUMENTS

| EP | 0282266 | 9/1988 |
|---|---|---|
| EP | 2164831 | 3/2010 |

OTHER PUBLICATIONS

International Search Report, issued in PCT/EP2009/056302, dated Sep. 25, 2009.
International Preliminary Report on Patentability, issued in PCT/EP2009/056302, dated Nov. 30, 2010.
Mansour et al., "Efficient Heterogeneously Catalyzed Amidocarbonylation of Bromoarenes Based on a Serinol-Derived Chelate Diphosphine Ligand", Journal of Molecular Catalysis A: Chemical, (2006), pp. 40-43, vol. 250.

* cited by examiner

*Primary Examiner* — Johann R Richter
*Assistant Examiner* — Pancham Bakshi
(74) *Attorney, Agent, or Firm* — Brinks Gilson & Lione

(57) ABSTRACT

Process for the preparation of aromatic and heteroaromatic carboxylic acids, carboxylic acid esters and carboxamides by the reaction of aromatic or heteroaromatic halides $R—X_n$, in which n=integer from 1 to 6, R=substituted or unsubstituted and aromatic or heteroaromatic radical and X=chlorine, bromine or iodine atom, with carbon monoxide and water, ammonia, alcohols or amines in the presence of bases and zero-valent or divalent palladium compounds and bidentate diphosphanes or complexes of zero-valent or divalent palladium with bidentate diphosphanes, in which use is made of bidentate diphosphanes $$(R^1—)(R^2—)P—Y—P(—R^3)(—R^4)$$

in which $R^1$ to $R^4$=unsubstituted aryl radicals or aryl radicals substituted with at least one radical exhibiting a positive resonance effect or a positive inductive effect, or unsubstituted or substituted cycloalkyl radicals, and Y=hydrocarbon group with a total of 2 to 20 carbon atoms, in which at least one of the carbon atoms carries only one or no hydrogen atom as substituent; except for the reaction of 4-bromo-3-difluoromethyl-1-methylpyrazole with 2-(3,4,5-trifluorophenyl) aniline and carbon monoxide to give N-[2-(3,4,5-trifluorophenyl)phenyl]-3-difluoromethyl-1-methylpyrazole-4-carboxamide.

35 Claims, No Drawings

METHOD FOR PRODUCING AROMATIC AND HETEROAROMATIC CARBOXYLIC ACIDS, CARBOXYLIC ACID ESTERS AND CARBOXYLIC ACID AMIDES

This application is a National Stage application of International Application No. PCT/EP2009/056302, filed May 25, 2009, the entire contents of which is hereby incorporated herein by reference. This application also claims priority under 35 U.S.C. §119 to European Patent Application No. 08156993.1, filed May 27, 2008, the entire contents of which is hereby incorporated herein by reference.

FIELD OF THE INVENTION

The present invention relates to a novel process for the preparation of aromatic and heteroaromatic carboxylic acids, carboxylic acid esters and carboxamides.

STATE OF THE ART

Process for the preparation of aromatic and heteroaromatic carboxylic acids, carboxylic acid esters and carboxamides by the reaction of aromatic or heteroaromatic halides of the general formula I:

$$R-X_n \quad (I),$$

in which the index and the variables have the following meanings:
n integer from 1 to 4,
R substituted or unsubstituted and aromatic or heteroaromatic radical and
X chlorine, bromine or iodine atom, in particular chlorine atom;
with carbon monoxide and water, ammonia, alcohols or amines in the presence of zero-valent or divalent palladium compounds, bidentate diphosphanes and bases are known from U.S. Pat. No. 5,344,961 or European patent application EP 0 282 266 A2.

Use is made, in U.S. Pat. No. 5,344,961, of bidentate diphosphanes of the general formula $$(R-)_2P-R'-P(-R)_2$$

in which the variables have the following meanings:
R aromatic radical with up to 15 carbon atoms, at least one aromatic ring of R being substituted with a radical which attracts electrons or exhibits a negative inductive effect, in particular alkyloxy or dialkylamino groups, and
R' linking hydrocarbon radical with up to 10, preferably from 2 to 4, carbon atoms.

Preferred radicals R are 2-methoxyphenyl, 2-propoxyphenyl, 2,4-diethoxyphenyl, 2-dimethylaminophenyl, 2-ethymethylaminophenyl and 2,4,6-trimethoxyphenyl, in particular 2-methoxyphenyl. Suitable radicals R' are 1,2-ethylene, 1,3-propylene, 1,4-butylene, 2,2-dimethyl-1,3-propylene and 2,3-dimethyl-1,4-butylene. However, use is preferably made of 1,3-[bis(2-methoxyphenyl)phosphanyl]propane. As emerges from the examples of the United States Patent, merely bromobenzene could be converted with carbon monoxide and alcohol in the presence of palladium acetate and 1,3-[bis(2-methoxyphenyl)phosphanyl]propane quantitatively to give ethyl benzoate, against which chlorobenzene was converted only up to approximately 10%. 4-Methoxychlorobenzene was even converted to ethyl 4-methoxybenzoate only up to 5%. If 1,3-[bis(2-methoxyphenyl)phosphanyl]propane was replaced by 1,3-bis(diphenylphosphanyl) propane, bromobenzene itself yielded, after 15 hours, only traces of ethyl benzoate.

European patent application EP 0 282 266 A2 proposes a series of diphosphanes for use in the abovementioned process. However, in examples 1 to 21, use is made exclusively of 1,4-bis(diphenylphosphanyl)butane. The yield of aromatic esters and amides is admittedly higher than in the process according to U.S. Pat. No. 5,344,961 but here also only low to moderate yields are achieved.

European patent application EP 0 282 266 A2 and U.S. Pat. No. 5,344,961 therefore do not suggest or indicate to a person skilled in the art how the yield of useful products could be significantly increased even in the case of aromatic chlorides.

A description is given, in the prior European patent application with the application number EP 07109463.5 of 1 Jun. 2007, of the reaction of 4-bromo-3-difluoromethyl-1-methylpyrazole with 2-(3,4,5-trifluorophenyl)aniline and carbon monoxide to give N-[2-(3,4,5-trifluorophenyl)phenyl]-3-difluoromethyl-1-methylpyrazole-4-carboxamide
(a) in N-methylpyrrolidone in the presence of $Pd(C_6H_5CN)_2Cl_2$, 2,2-dimethyl-1,3-bis(diphenylphosphanyl)propane and potassium carbonate or
(b) in acetonitrile in the presence of $Pd(C_6H_5CN)_2Cl_2$, 3,3-bis(diphenylphosphanyl-methylene)heptane, triethylamine and potassium carbonate.

In the prior European patent application, 2,2-dimethyl-1,3-bis(diphenylphosphanyl)-propane is described as Pepstar and bis(diphenylphosphanylmethylene)heptane is described as Et,Bu-Pepstar.

OBJECT

It is therefore the object of the present invention to make available a novel alternative process of the type mentioned at the start which, not only in the case of aromatic bromides but also in the case of aromatic and heteroaromatic chlorides, yields aromatic and heteroaromatic carboxylic acid esters and carboxamides in especially high yields, in particular virtually quantitative or quantitative yields. Furthermore, the novel process should make it possible to prepare, even in the case of aromatic and heteroaromatic chlorides, aromatic and heteroaromatic carboxylic acids in especially high yield, in particular virtually quantitative or quantitative yield.

Solution According to the Invention

We have found that the novel process for the preparation of aromatic and heteroaromatic carboxylic acids, carboxylic acid esters and carboxamides is achieved by the reaction of aromatic or heteroaromatic halides of the general formula I:

$$R-X_n \quad (I),$$

in which the index and the variables have the following meanings:
n integer from 1 to 6,
R substituted or unsubstituted and aromatic or heteroaromatic radical and
X chlorine, bromine or iodine atom;
with carbon monoxide and water, ammonia, alcohols or amines in the presence of bases and zero-valent or divalent palladium compounds and bidentate diphosphanes or complexes of zero- or divalent palladium with bidentate diphosphanes, in which use is made of bidentate diphosphanes of the general formula II:

$$(R^1-)(R^2-)P-Y-P(-R^3)(-R^4) \quad (II),$$

in which the variables have the following meanings:
$R^1$ to $R^4$ independently of one another, identically or differently, unsubstituted aryl radicals or aryl radicals substituted with at least one radical exhibiting a positive resonance effect or a positive inductive effect, or unsubstituted or substituted cycloalkyl radicals; and Y hydrocarbon group with a total of 2 to 20 carbon atoms, in which at least one of the carbon atoms carries only one or no hydrogen atom as substituent;

except for the reaction of 4-bromo-3-difluoromethyl-1-methylpyrazole with 2-(3,4,5-trifluorophenyl)aniline and carbon monoxide to give N-[2-(3,4,5-trifluorophenyl)phenyl]-3-difluoromethyl-1-methylpyrazole-4-carboxamide, (a) in N-methylpyrrolidone in the presence of $Pd(C_6H_5CN)_2Cl_2$, 2,2-dimethyl-1,3-bis(diphenylphosphanyl)propane and potassium carbonate or (b) in acetonitrile in the presence of $Pd(C_6H_5CN)_2Cl_2$, 3,3-bis(diphenylphosphanylmethylene)heptane, triethylamine and potassium carbonate.

The novel process for the preparation of aromatic and heteroaromatic carboxylic acids, carboxylic acid esters and carboxamides is described below as "process according to the invention".

Advantages of the Invention

In view of the state of the art, it was surprising and, for a person skilled in the art, not foreseeable that the object underlying the present invention could be achieved with the help of the process according to the invention.

In particular, it was surprising that the process according to the invention, not only in the case of aromatic bromides but also in the case of aromatic and heteroaromatic chlorides, yielded aromatic and heteroaromatic carboxylic acid esters and carboxamides in especially high yields, in particular virtually quantitative or quantitative yields. Furthermore, the novel process made it possible to prepare, even in the case of aromatic and heteroaromatic chlorides, aromatic and heteroaromatic carboxylic acids in especially high yield, in particular virtually quantitative or quantitative yield.

DETAILED DESCRIPTION OF THE INVENTION

The use of bidentate diphosphanes of the general formula II:

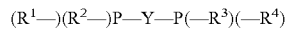

$(R^1—)(R^2—)P—Y—P(—R^3)(—R^4)$ is essential for the process according to the invention.

In the context of the present invention, the IUPAC nomenclature is used for the description of the bidentate diphosphanes II (cf. Römpp Online 2008, "Phosphanes"). Furthermore, in the context of the present invention, for the description of the bidentate diphosphanes II, for the sake of simplicity and clarity, the basic structure is based on the propane chain or the 1,3-propylene radical substituted in the 2-position or 2,2-positions, even if this conflicts in the isolated case with the IUPAC rules.

In the context of the present invention, use is made of inert substituents and linking groups, i.e. substituents and linking groups which, under the conditions of the process according to the invention, do not react and/or initiate and/or catalyze decomposition reactions with any of the starting materials and final products produced in this connection. The inert substituents can, however, cause inductive effects and/or resonance effects.

In the general formula II, the radicals $R^1$ to $R^4$ are, independently of one another, identical or different and are unsubstituted aryl radicals or aryl radicals substituted with at least one radical which exhibits a positive resonance effect, i.e. a +M effect, or a positive inductive effect, i.e. a +I effect, or unsubstituted or substituted cycloalkyl radicals.

Reference is made, for the terms "positive resonance effect" or "+M effect", to Römpp Online 2008, "Resonance", and, for the terms "positive inductive effect" or "+I effect", to Römpp Online 2008, "Inductive effect".

The radical exhibiting a positive resonance effect, i.e. a +M effect, or a positive inductive effect, i.e. a +I effect, is preferably inert in the sense described above.

Examples of suitable radicals which cause a +M effect are amino groups and hydroxyl groups, provided that they are inert under the conditions of a given process according to the invention.

Examples of suitable radicals causing a +I effect are the branched or unbranched alkyl radicals with one carbon atom or with from 2 to 12 carbon atoms described above.

The substituted and unsubstituted aryl radicals preferably exhibit from 6 to 20 carbon atoms in the ring or in the rings.

The radicals $R^1$ to $R^4$ are preferably chosen from the group consisting of unsubstituted phenyl and naphthyl and substituted phenyl and naphthyl which are substituted with at least one radical exhibiting a positive resonance effect or a positive inductive effect. Use is made in particular of unsubstituted phenyl.

The unsubstituted and substituted cycloalkyl radicals $R^1$ to $R^4$ preferably exhibit from 5 to 16 carbon atoms in the ring or in the rings. Use is preferably made of cyclopentyl and cyclohexyl, in particular cyclohexyl.

The substituents of the substituted cycloalkyl radicals $R^1$ to $R^4$ are preferably chosen from the group consisting of fluorine atom, chlorine atom, bromine atom, nitrile group, nitro group and also substituent which comprises or consists of at least one nonhalogenated, partially halogenated or perhalogenated, in particular nonfluorinated, partially fluorinated and perfluorinated, unbranched or branched alkyl radical with up to 12 carbon atoms, at least one nonhalogenated, partially halogenated or perhalogenated, in particular nonfluorinated, partially fluorinated and perfluorinated, cycloalkyl radical with from 3 to 16 carbon atoms and/or at least one nonfluorinated, partially fluorinated and perfluorinated aryl radical with from 6 to 20 carbon atoms. In this connection, the substituent can be bonded as such, via a carbon-carbon single bond or an inert divalent functional group, to at least one of the radicals $R^1$ to $R^4$.

The inert divalent functional group is preferably chosen from the group consisting of ether, thioether, carboxylic acid ester, thiocarboxylic acid ester, carbonate, thiocarbonate, phosphoric acid ester, thiophosphoric acid ester, phosphonic acid ester, thiophosphonic acid ester, phosphite, thiophosphite, sulfonic acid ester, amide, amine, thioamide, phosphoric acid amide, thiophosphoric acid amide, phosphonic acid amide, thiophosphonic acid amide, sulfonic acid amide, imide, hydrazide, urethane, urea, thiourea, carbonyl, thiocarbonyl, sulfone or sulfoxide groups.

The radicals $R^1$ to $R^4$ are in particular unsubstituted phenyl and cyclohexyl radicals.

In the general formula II, the variable Y is a hydrocarbon group with a total of 2 to 20, preferably 3 to 16 and in particular 3 to 10 carbon atoms, at least one, preferably one, of the carbon atoms carrying only one or no, preferably no, hydrogen atom as substituent.

The hydrocarbon groups Y comprise carbon atoms and hydrogen atoms or they consist exclusively of these. Preferably, they consist exclusively of carbon atoms and hydrogen atoms.

The hydrocarbon groups Y can comprise aromatic groups or cycloaliphatic groups.

The hydrocarbon groups Y can be substituted and unsubstituted.
Examples of suitable hydrocarbon groups Y are ethylidene, propylidene, butylidene, 1,2- and 1,3-cyclopentylene, cyclopentylidene, 1,2-, 1,3- and 1,4-cyclohexylene, cyclohexylidene or the divalent hydrocarbon groups present in the structures Ya) to Yv):
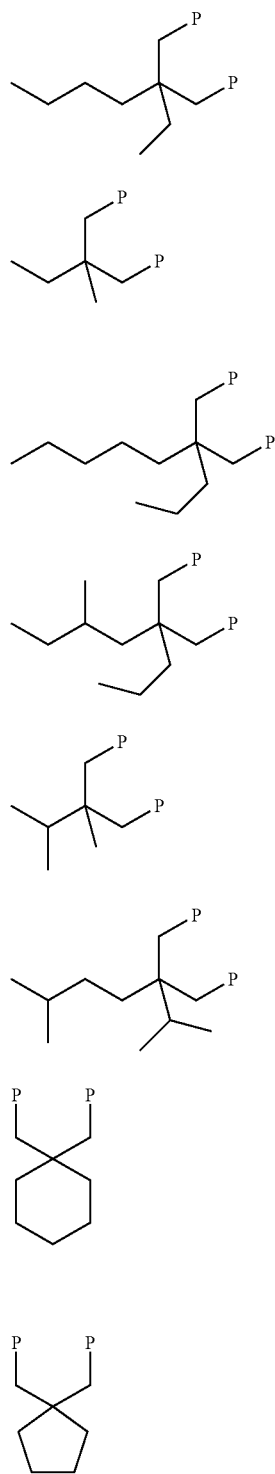
a)
b)
c)
d)
e)
f)
g)
h)
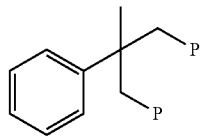
i)
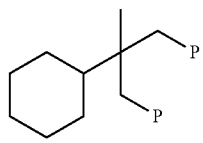
j)
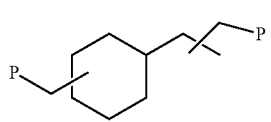
k)
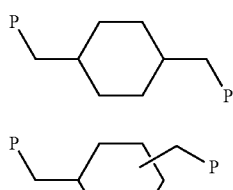
l)
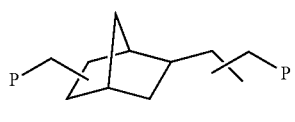
m)
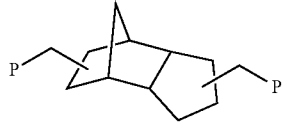
n)
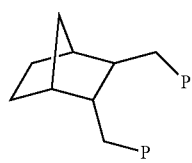
o)
p)
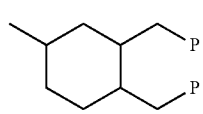
q)
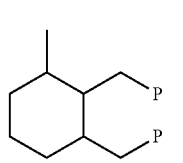
r)
s)
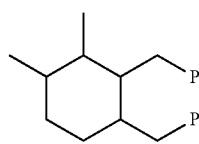
t)

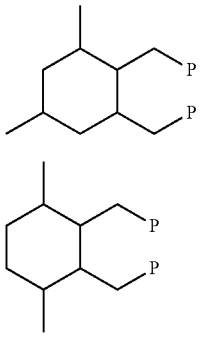

u)

v)

Examples of diphosphanes II with chiral hydrocarbon groups Y, such as (+)-NORPHOS, (R,R)-CHIRAPHOS or (−)-Diop, are known from Thieme Römpp Online 2008, "Phosphanes".

Use is particularly preferably made of hydrocarbon groups Y of the general formula III:

—C(—R$^7$)$_2$—C(—R$^5$)(—R$^6$)—C(R$^7$)$_2$—  (III).

In the general formula III, the variables R$^5$ and R$^6$ are, independently of one another, identical or different and are hydrogen atoms, substituted or unsubstituted and linear or branched alkyl radicals, substituted or unsubstituted cycloalkyl radicals or aryl radicals or radicals comprising or consisting of at least two of these radicals, only one of the radicals R$^5$ and R$^6$ being a hydrogen atom.

Use may be made, as substituents for the substituted radicals R$^5$ and R$^6$, of the substituents described above with the radicals R$^1$ and R$^4$. The substituents can be bonded to the radicals R$^5$ and R$^6$ via covalent bonds or the inert divalent linking groups described below.

Preferably, in a given bidentate diphosphane II, neither of the radicals R$^5$ or R$^6$ is a hydrogen atom.

Provided that neither of the radicals R$^5$ or R$^6$ is a hydrogen atom, they can be linked to one another cyclically. In this connection, the linking can take place via a carbon-carbon single bond or an inert divalent linking group preferably chosen from the group consisting of alkylene, cycloalkylene, arylene, ether, thioether, carboxylic acid ester, thiocarboxylic acid ester, carbonate, thiocarbonate, phosphoric acid ester, thiophosphoric acid ester, phosphonic acid ester, thiophosphonic acid ester, phosphite, thiophosphite, sulfonic acid ester, amide, amine, thioamide, phosphoric acid amide, thiophosphoric acid amide, phosphonic acid amide, thiophosphonic acid amide, sulfonic acid amide, imide, hydrazide, urethane, urea, thiourea, carbonyl, thiocarbonyl, sulfone or sulfoxide groups.

The radicals R$^5$ and R$^6$ are preferably chosen from the group consisting of substituted and unsubstituted, preferably unsubstituted, linear or branched alkyl radicals with one carbon atom or from 2 to 12 carbon atoms, in particular unsubstituted alkyl radicals with one carbon atom or from 2 to 6 carbon atoms;

substituted and unsubstituted cycloalkyl radicals with from 5 to 16 carbon atoms in the ring or in the rings, in particular unsubstituted cycloalkyl radicals and cycloalkyl radicals substituted with alkyl radicals, preferably alkyl radicals with from 1 to 4 carbon atoms, the cycloalkyl radicals having from 5 to 16 carbon atoms in the ring or in the rings;

substituted and unsubstituted aryl radicals with from 6 to 20 carbon atoms in the ring or in the rings, in particular unsubstituted aryl radicals and aryl radicals substituted with alkyl radicals, preferably alkyl radicals with from 1 to 4 carbon atoms, these aryl radicals having from 6 to 20 carbon atoms in the ring or in the rings;

substituted and unsubstituted x-cycloalkylalkan-1-yl radicals with from 5 to 16 carbon atoms in the cycloalkyl radical, in particular unsubstituted cycloalkyl radicals and cycloalkyl radicals substituted with alkyl radicals, preferably alkyl radicals with from 1 to 4 carbon atoms, the cycloalkyl radicals having from 5 to 16 carbon atoms in the cycloalkyl radical, and also with in each case one carbon atom or from 2 to 6 carbon atoms in the 1,x-alkylene radical of the x-cycloalkylalkane-1-yl radical, in which x=integer from 1 to 6, preferably from 1 to 4;

substituted and unsubstituted x-arylalkan-1-yl radicals with from 6 to 20 carbon atoms in the aryl radical, in particular unsubstituted aryl radicals and aryl radicals substituted with alkyl radicals, preferably alkyl radicals with from 1 to 4 carbon atoms, the aryl radicals having from 6 to 20 carbon atoms in the aryl radical, and also with in each case one carbon atom or from 2 to 6 carbon atoms in the 1,x-alkylene radical of the x-arylalkan-1-yl radical, in which x=integer from 1 to 6, preferably from 1 to 4; or substituted and unsubstituted y-arylcycloalkan-1-yl radicals with from 6 to 20 carbon atoms in the aryl radical and from 5 to 16 carbon atoms in the 1,y-cycloalkylene radical of the y-arylcycloalkan-1-yl radical, in particular unsubstituted aryl radicals and aryl radicals substituted with alkyl radicals, preferably alkyl radicals with from 1 to 4 carbon atoms, these aryl radicals having from 6 to 20 carbon atoms in the aryl radical, and cycloalkyl radicals with from 5 to 16 carbon atoms in the cycloalkyl radical, in which y=integer from 1 to 12, preferably from 1 to 4.

The linear or branched alkyl radicals R$^5$ and R$^6$ are preferably chosen from the group consisting of methyl, ethyl, propyl, isopropyl, n-butyl, sec-butyl, tert-butyl, n-pentyl, isopentyl, neopentyl, n-hexyl, n-heptyl, n-octyl, 2,2-dimethylhexyl, 3-methyl-2-ethyl-pentyl, nonyl, decyl, 5-methylnonyl, undecyl and dodecyl.

The cycloalkyl radicals R$^5$ and R$^6$ are preferably chosen from the group consisting of cyclopentyl and cyclohexyl and also the radicals which are derived from norcarane, norpinane, norbornane, bornane, 10-norbornane, o-menthane, m-menthane, p-menthane, thujane, carane, pinane, 2-ethylpinane, 2,4,7,7-tetramethylnorcarane and 2,2-dimethylnorbornane and are linked via a ring carbon atom to the basic structure of the general formula II, i.e. to the 2-position or 2,2-positions of the 1,3-propylene radical.

The x-cycloalkylalkan-1-yl radicals R$^5$ and R$^6$ are preferably chosen from the group consisting of cyclohexylmethyl, 2-cyclohexyleth-1-yl, 3-cyclohexylprop-1-yl and 4-cyclohexylbut-1-yl and also the radicals which are derived from bornane, 10-norbornane, o-menthane, m-menthane, p-menthane, thujane, carane, pinane, 2-ethylpinane, 2,4,7,7-tetramethylnorcarane and 2,2-dimethylnorbornane and are linked, via an aliphatic hydrocarbon atom not occurring in the ring, to the basic structure of the general formula II.

The aryl radicals R$^5$ and R$^6$ are preferably chosen from the group consisting of phenyl and naphthyl and also the radicals which are derived from toluene, xylene, propylbenzene, isopropylbenzene, n-butylbenzene, sec-butylbenzene and tert-butylbenzene and are linked via an aromatic ring carbon atom to the basic structure of the general formula II.

The x-arylalkan-1-yl radicals $R^5$ and $R^6$ are preferably chosen from the group consisting of the radicals which are derived from toluene, xylene, propylbenzene, isopropylbenzene, n-butylbenzene, sec-butylbenzene and tert-butylbenzene and are linked, via an aliphatic carbon atom not occurring in the ring, to the basic structure of the general formula II.

The y-arylcycloalkan-1-yl radicals $R^5$ and $R^6$ are preferably chosen from the group consisting of the radicals which are derived from phenylcyclopentane, phenylcyclohexane, tolylcyclohexane and xylylcyclohexane and are linked, via a carbon atom occurring in the cycloalkane ring, to the basic structure of the general formula II.

The radicals $R^5$ and $R^6$ are particularly preferably chosen from the group consisting of methyl, ethyl, propyl, n-butyl, n-pentyl, n-hexyl, benzyl, cyclopentyl, cyclohexyl and phenyl, very particularly preferably methyl, ethyl, propyl, n-butyl, n-pentyl, n-hexyl, cyclohexyl and phenyl, in particular methyl, ethyl and n-butyl.

Use is preferably made of unsubstituted radicals $R^5$ and $R^6$.

In the general formula III, the variable $R^7$ is chosen from the group consisting of hydrogen atoms, fluorine atoms, chlorine atoms, bromine atoms, nitrile groups, nitro groups and radicals $R^5$ and $R^6$.

If the radicals $R^7$ are radicals $R^5$ and $R^6$, they can be bonded, via covalent linkages or the inert divalent linking groups described above, to the carbon atoms of the basic structure of the general formula III, i.e. the 1,3-propane radical.

The hydrocarbon group Y of the general formula III can comprise from 1 to 4 radicals $R^7$. In this connection, at least two of the radicals $R^7$ can be identical or different from one another. Preferably, one, preferably two and preferably three of the radicals $R^7$ and in particular all four radicals $R^7$ are a hydrogen atom or hydrogen atoms.

The bidentate diphosphanes of the general formula II are preferably chosen from the group consisting of
2-methyl-, 2-ethyl-, 2-propyl-, 2-(n-butyl)-, 2-(n-pentyl)-, 2-(n-hexyl)-, 2-cyclohexyl- and 2-phenyl-1,3-bis(diphenylphosphanyl)propane and -1,3-bis(dicyclohexylphosphanyl)propane,
2,2-dimethyl-, 2,2-diethyl-, 2,2-dipropyl-, 2,2-di(n-butyl)-, 2,2-di(n-pentyl)-, 2,2-di(n-hexyl)-, 2,2-dicyclohexyl- and 2,2-diphenyl-1,3-bis(diphenylphosphanyl)propane and -1,3-bis(dicyclohexylphosphanyl)propane,
2-methyl-2-ethyl-, -2-propyl-, -2-(n-butyl)-, -2-(n-pentyl)-, -2-(n-hexyl)-, -2-cyclohexyl- and -2-phenyl-1,3-bis(diphenylphosphanyl)propane and -1,3-bis(dicyclohexylphosphanyl)propane,
2-ethyl-2-propyl-, -2-(n-butyl)-, -2-(n-pentyl)-, -2-(n-hexyl)-, -2-cyclohexyl- and -2-phenyl-1,3-bis(diphenylphosphanyl)propane and -1,3-bis(dicyclohexylphosphanyl)propane,
2-propyl-2-(n-butyl)-, -2-(n-pentyl)-, -2-(n-hexyl)-, -2-cyclohexyl- and -2-phenyl-1,3-bis(diphenylphosphanyl)propane and -1,3-bis(dicyclohexylphosphanyl)propane,
2-(n-butyl)-2-(n-pentyl)-, -2-(n-hexyl)-, -2-cyclohexyl- and -2-phenyl-1,3-bis(diphenylphosphanyl)propane and -1,3-bis(dicyclohexylphosphanyl)propane,
2-(n-pentyl)-2-(n-hexyl)-, -2-cyclohexyl- and -2-phenyl-1,3-bis(diphenylphosphanyl)propane and -1,3-bis(dicyclohexylphosphanyl)propane,
2-(n-hexyl)-2-cyclohexyl- and -2-phenyl-1,3-bis(diphenylphosphanyl)propane and -1,3-bis(dicyclohexylphosphanyl)propane and
2-cyclohexyl-2-phenyl-1,3-bis(diphenylphosphanyl)propane and -1,3-bis(dicyclohexylphosphanyl)propane.

Use is made in particular of 2-ethyl-2-butyl- or 2,2-dimethyl-1,3-bis(diphenylphosphanyl)propane or mixtures from these. 2,2-dimethyl-1,3-bis(diphenylphosphanyl)propane is subsequently described as Pepstar and 2-ethyl-2-butyl-bis (diphenylphosphanyl)propane is subsequently described as Bustar.

The diphosphanes II are prepared with the help of conventional and known processes of organophosphorus chemistry, preferably by the reaction of a suitable dicycloalkylfluoro-, -chloro- or -bromophosphane or a suitable dicycloarylalkoxy- or -aryloxyphosphane or a dicycloalkylalkoxy- or -aryloxyphosphane, in particular a suitable dicycloalkylchloro- or -bromophosphane, such as, e.g., dicyclohexylchlorophosphane or -bromophosphane, with a suitable 1,3-difluoro-, 1,3-dichloro-, 1,3-bromochloro-, 1,3-chlorofluoro-, 1,3-bromofluoro- or 1,3-dibromopropane, in particular 1,3-dichloro-, 1,3-bromochloro- or 1,3-dibromopropane, such as, e.g.,
1,3-dichloro-, 1,3-bromochloro- or 1,3-dibromo-2-methyl-, -2-ethyl-, -2-propyl-, -2-(n-butyl)-, -2-(n-pentyl)-, -2-(n-hexyl)-, -2-cyclohexyl- and -2-phenylpropane;
1,3-dichloro-, 1,3-bromochloro- or 1,3-dibromo-2,2-dimethyl-, -2,2-diethyl-, -2,2-dipropyl-, -2,2-di(n-butyl)-, -2,2-di(n-pentyl)-, -2,2-di(n-hexyl)-, -2,2-dicyclohexyl- and -2,2-diphenylpropane;
1,3-dichloro-, 1,3-bromochloro- or 1,3-dibromo-2-methyl-2-ethyl-, -2-propyl-, -2-(n-butyl)-, -2-(n-pentyl)-, -2-(n-hexyl)-, -2-cyclohexyl- and -2-phenylpropane;
1,3-dichloro-, 1,3-bromochloro- or 1,3-dibromo-2-ethyl-2-propyl-, -2-(n-butyl)-, -2-(n-pentyl)-, -2-(n-hexyl)-, -2-cyclohexyl- and -2-phenylpropane;
1,3-dichloro-, 1,3-bromochloro- or 1,3-dibromo-2-propyl-2-(n-butyl)-, -2-(n-pentyl)-, -2-(n-hexyl)-, -2-cyclohexyl- and -2-phenylpropane;
1,3-dichloro-, 1,3-bromochloro- or 1,3-dibromo-2-(n-butyl)-2-(n-pentyl)-, -2-(n-hexyl)- and -2-cyclohexylpropane; -2-(n-pentyl)-2-(n-hexyl)-, -2-cyclohexyl-1,3 and -2-phenyl-1,3-propane; -2-(n-hexyl)-2-cyclohexyl- and -2-phenyl-1,3-propane; and
1,3-dichloro-, 1,3-bromochloro- or 1,3-dibromo-2-cyclohexyl-2-phenylpropane;
in particular 1,3-dichloro-2,2-dimethylpropane, by elimination of the halogen atoms with metallic sodium. Use is preferably made, in this connection, of the reaction conditions described in international patent application WO 2006/084878 A1 or in L. Brandsma et al., "Application of Transition Metal Catalysts in Organic Synthesis", Springer-Verlag, Berlin 1997, pages 6 to 9.

Aromatic or heteroaromatic halides of the general formula I are reacted in the process according to the invention.

In the general formula I R(—X)$_n$, the index n is an integer from 1 to 6, preferably from 1 to 4, preferably from 1 to 3 and in particular 1 or 2.

The variable X is a chlorine, bromine or iodine atom, preferably a chlorine or bromine atom, in particular a chlorine atom.

The variable R is a substituted or unsubstituted and aromatic or heteroaromatic radical.

The aromatic radicals R are preferably derived from benzene and from polycyclic aromatic hydrocarbons. The heteroaromatic radicals R are preferably derived from monocyclic and polycyclic aromatic heterocycles.

The polycyclic aromatic hydrocarbons are preferably chosen from the group consisting of
hydrocarbons, in which at least two benzene nuclei, at least two fused polycyclic aromatic hydrocarbons or at least one benzene nucleus and at least one fused polycyclic aromatic hydrocarbon are linked to one another via at least one carbon-carbon single bond, and
fused polycyclic aromatic hydrocarbons.

The polycyclic aromatic hydrocarbons are particularly preferably chosen from the group consisting of biphenyl, the isomeric triphenylenes, quaterphenylenes, quinquephenylenes, phenylnaphthalenes and binaphthalenes, biphenylene, asymmetrical and symmetrical indacene, fluorene, naphthalene, acenaphthylene, acenaphthene, phenanthrene, anthracene, chrysene, pyrene, fluoranthene, benz[a]anthracene, benzo[k]fluoranthene, benzo[b]fluoranthene, benzo[a]pyrene, dibenz[a:h]anthracene, benzo[g:h:i]perylene and indeno[1,2,3-c:d]pyrene, tetrabenzonaphthalene and phenanthro[3,4-c]phene.

The aromatic radicals R are derived in particular from benzene or naphthalene, in particular benzene.

The aromatic heterocycles preferably comprise at least one heteroatom chosen from the group consisting of nitrogen atom, oxygen atom and sulfur atom.

The aromatic heterocycles are preferably chosen from the group consisting of pyrrole, imidazole, pyrazole, the isomeric isothiazoles and isoxazoles, pyridine, pyrazine, pyrimidine, pyridazine, 1H-pyrrolizine, indolizine, isoindole, indole, 1H-indazole, purine, 4H-quinolizine, isoquinoline, quinoline, phthalazine, 1,8-naphthyridine, quinoxaline, quinazoline, cinnoline, pteridinine, carbazole, beta-carboline, phenanthridine, acridine, perimidine, 1,7-phenanthroline, phenazine, phenothiazine, phenoxazine, thiophene, benzo[b]thiophene, naphtho[2,3-b]thiophene, thianthrene, furan, isobenzofuran, phenoxazine, thiophthene, thiophanthrene, thianaphthene, coumarone, isocoumarone, indoxazene, anthranil and piazthiole.

The radical can be substituted with at least one inert substituent in the sense described above. The substituent is preferably chosen from the group consisting of fluorine atom, nitrile group, nitro group and substituent which comprises or consists of at least one nonhalogenated, partially halogenated or perhalogenated and unbranched or branched alkyl radical with up to 16 carbon atoms, at least one nonhalogenated, partially halogenated or perhalogenated cycloalkyl radical with up to 16 carbon atoms and/or at least one nonfluorinated, partially fluorinated and perfluorinated aryl radical with from 6 to 20 carbon atoms. In this connection, the substituent can be bonded as such to the radical R via a carbon-carbon single bond or an inert divalent functional group and/or the alkyl radicals, cycloalkyl radicals and/or aryl radicals in such a substituent can be bonded to one another via at least one carbon-carbon single bond and/or at least one inert divalent functional group.

The inert divalent functional group is preferably chosen from the group consisting of ether, thioether, carboxylic acid ester, thiocarboxylic acid ester, carbonate, thiocarbonate, phosphoric acid ester, thiophosphoric acid ester, phosphonic acid ester, thiophosphonic acid ester, phosphite, thiophosphite, sulfonic acid ester, amide, amine, thioamide, phosphoric acid amide, thiophosphoric acid amide, phosphonic acid amide, thiophosphonic acid amide, sulfonic acid amide, imide, hydrazide, urethane, urea, thiourea, carbonyl, thiocarbonyl, sulfone or sulfoxide groups, in particular ether, carboxylic acid ester, amide and carbonyl groups.

Examples of satisfactorily suitable aromatic and heteroaromatic halides of the general formula I are known from European patent application EP 0 282 266 A2, page 5, line 40, to page 6, line 5. Reference is expressly made here to the passage.

Examples of suitable aromatic and heteroaromatic halides of the general formula I which are particularly suitable are chlorobenzene, bromobenzene, 2-, 3- and 4-chloro- and -bromoacetophenone, methyl and ethyl 2-, 3- and 4-chloro- and -bromobenzoate, 2-, 3- and 4-chloro- and -bromobenzaldehyde, 2-, 3- and 4-chloro- and -bromoanisol, 2-, 3- and 4-chloro- and -bromotoluene, 2-, 3- and 4-chloro- and -bromobenzonitrile, 2-, 3- and 4-chloro- and -bromonitrobenzene, 2-, 3- and 4-chloro- and -bromofluorbenzene, 2-, 3- and 4-chloro- and -bromotrifluoromethylbenzene, 1- and 2-chloro- and -bromonaphthalene, 1-chloro- and -bromo-2-, -3-, -4-, -5-, -6-, -7- and -8-methoxynaphthalene, 2-chloro- and -bromo-1-, -3-, -4-, -5-, -6-, -7- and -8-methoxynaphthalene, 2-, 3- and 4-chloro- and -bromobiphenyl, 9-chloro- and -bromophenanthrene, 1,2-, 1,3- and 1,4-dichlorobenzene, 1,2,3-, 1,2,4- and 1,3,5-trichlorobenzene, 1,2,3,4-, 1,2,3,5- and 1,2,4,5-tetrachlorobenzene, 3-, 4- and 5-chloro- and -bromopyrazole, 2-, 3- and 4-chloro- and -bromopyridine, 2- and 3-chloro- and -bromothiophene, 2,3-, 2,4-, 2,5- and 2,6-dichloro- and -dibromopyridine, 2,3-, 2,4- and 2,5-dichloro- and -dibromothiophene, 2,3-, 2,4-, 2,5-, 2,6-, 2,5-, 2,6-, 2,7- and 2,8-dichloro- and -dibromoquinoline, 3,4-, 3,5-, 3,6-, 3,7- and 3,8-dichloro- and -dibromoquinoline, 4,5-, 4,6-, 4,7- and 4,8-dichloro- and -dibromoquinoline, 5,6-, 5,7- and 5,8-dichloro- and -dibromoquinoline, 6,7- and 6,8-dichloro- and -dibromoquinoline, and 7,8-dichloro- and -dibromoquinoline.

The aromatic and heteroaromatic halides of the general formula I described above can be used in molar excess both as starting materials and as solvents, provided that they are liquid under the reaction conditions employed.

In the process according to the invention, the aromatic and heteroaromatic halides of the general formula I described above are reacted with water to give carboxylic acids, with ammonia to give primary amides, with alcohols to give carboxylic acid esters and with amines to give secondary and tertiary amides.

The alcohol is preferably chosen from the group consisting of aliphatic, cycloaliphatic, aromatic and heteroaromatic alcohols with from 1 to 4 hydroxyl groups in the molecule.

The aliphatic alcohol is preferably chosen from the group consisting of methanol, ethanol, propanol, isopropanol, n-butanol, sec-butanol, tert-butanol, n-amyl alcohol, 2-methyl-2-butanol, n-hexanol, the isomeric heptanols, 4-methyl-3-heptanol, the isomeric capryl alcohols, nonanols and decanols, benzyl alcohol, 2-phenylethanol, 3-phenylpropanol, 4-phenylbutanol, ethylene glycol, propylene glycol, the isomeric butanediols, polyethylene glycols, polypropylene glycols and diethyloctanediols, N-phenyldiethanolamine, glycerol, trimethylolethane, trimethylolpropane, triethanolamine, erythritol, threitol and pentaerythritol.

The cycloaliphatic alcohol is preferably chosen from the group consisting of cyclopentanol, cyclohexanol, borneol, isoborneol, 1,1-, 1,2-, 1,3- and 1,4-cyclohexanediol, cis- and trans-1,8-terpin and hydrogenated bisphenol A and F.

The aromatic alcohol is preferably chosen from the group consisting of phenol, pyrocatechol, resorcinol, hydroquinone, pyrogallol, phloroglucinol, α- and β-naphthol, and bisphenol A and F.

The heteroaromatic alcohol is preferably chosen from the group consisting of the isomeric hydroxypyridines, hydroxypyrazines, hydroxypyrimidines, hydroxypyridazines, 1H-hydroxypyrrolizines, 4H-hydroxyquinolizines, hydroxyisoquinolines, hydroxyquinolines, hydroxyphthalazines, hydroxy-1,8-naphthyridines, hydroxyquinoxalines, hydroxyquinazolines, hydroxyquinolines, hydroxypteridines, hydroxyphenanthridines, hydroxyacridines and hydroxy-1,7-phenanthrolines and also allupurinol.

The alcohols described above can be used as such or in the form of alkoxides, in which they at the same time take on the function of the base.

The amine is preferably chosen from the group consisting of aliphatic, cycloaliphatic, cyclic, aromatic and heteroaromatic primary and secondary amines with from 1 to 4 amino groups in the molecule.

The aliphatic or cycloaliphatic and primary or secondary amine is preferably chosen from the group consisting of methylamine, ethylamine, propylamine, isopropylamine, the isomeric butylamines, pentylamines, hexylamines, heptylamines, octylamines, nonylamines and decylamines, dodecylamine, benzylamine, the phenylethanamines, hydrazine, 1,2-ethylenediamine, 1,3-diaminopropane, putrescine, cadaverine, 1,6-diaminohexane, diethylenetriamine, triethylenetetramine, spermine, cyclohexylamine and dicyclohexylamine.

The cyclic secondary amine is preferably chosen from the group consisting of pyrrole, imidazole, pyrazole, isoindole, pyrrolidine, piperidine, morpholine, isoindoline, imidazolidine, pyrazolidine and piperazine.

The aromatic and heteroaromatic primary and secondary amines are preferably chosen from the group consisting of aniline, the isomeric phenylenediamines, diphenylamine, the isomeric biphenyldiamines, biphenyltriamines and biphenyltetramines, indole, indoline, 1H-indazole, purine, carbazole, β-carboline, perimidine, phenothiazine, the isomeric aminopyridines, aminopyrazines, aminopyrimidines, aminopyridazines, 1H-aminopyrrolizines, 4H-aminoquinolizines, aminoisoquinolines, aminoquinolines, aminophthalazines, amino-1,8-naphthyridines, aminoquinoxalines, aminoquinazolines, aminocinnolines, aminopteridines, aminophenanthridines, aminoacridines and amino-1,7-phenanthrolines, benzoguanamine and melamine.

The amines described above can be used in molar excess both as starting materials and as bases.

The respective parent substance of the alcohols and/or of the amines can be substituted with at least one inert substituent. The inert substituent is preferably chosen from the group consisting of the substituents described above.

The process according to the invention is carried out in the presence of at least one zero- or divalent palladium compound.

The zero-valent palladium compound is preferably chosen from the group consisting of metallic palladium and organopalladium(0) compounds and the divalent palladium compound is chosen from the group consisting of organopalladium(II) compounds and palladium(II) salts.

The metallic palladium is preferably supported. Examples of suitable carriers which are inert in the sense described above are active charcoal, aluminum oxide and aluminates, silicon dioxide and silicates, barium sulfate and calcium carbonate. When the metallic palladium is employed, use is also preferably made of conventional and known ligands which are able to complex palladium(0) compounds.

The organopalladium(0) compound is preferably chosen from the group consisting of tris($\eta^2$-alkene)palladium(0), bis(carbene)palladium(0), palladium(0)-phosphane complexes and mixed palladium(0)-($\eta^2$-alkene)-phosphane complexes.

The organopalladium(II) compound is preferably chosen from the group consisting of palladium(II)-chelate complexes, donor adducts with monovalent ligands or complexes with monovalent ligands and halides and π-bonded ligands.

The palladium(II) salt is preferably chosen from the group consisting of palladium(II) halides and carboxlyates.

Examples of suitable zero-valent and divalent palladium compounds are known from Hollemann-Wiberg, Lehrbuch der Anorganischen Chemie [Textbook of Inorganic Chemistry], Nils Wiberg, 102nd edition, 2007, "2.2 Verbindungen des Palladiums and Platins [Palladium and platinum compounds]", pages 1726 to 1743, in particular "2.2.6 Organische Verbindungen des Palladiums and Platins [Organic palladium and platinum compounds]", pages 1739 to 1734. Reference is expressly made here to these passages.

Use is preferably made of palladium(II) chloride, palladium(II) acetate, palladium(II) acetylacetonate, dichlorobis(cyanophenyl)palladium(II), dichlorobis(diphenylphosphanyl)-palladium(II) and/or tetrakis(diphenylphosphanyl)palladium(II), in particular palladium(II) acetate.

The palladium compounds can be used as such in the reaction according to the invention. However, it is also possible to convert them beforehand, with the diphosphanes II, in a way known per se, to palladium(0)- or palladium(II)-diphosphane complexes. The resulting complexes can then be used in the reaction according to the invention. Examples of suitable complexes which are highly satisfactory are Pd[2,2-dimethyl-1,3-bis(diphenylphosphanyl)propane]$_2$Cl$_2$ or Pd(Pepstar)$_2$Cl$_2$ and Pd[2-ethyl-2-butyl-bis(diphenylphosphanyl)propane]$_2$Cl$_2$ or Pd(Bustar)$_2$Cl$_2$.

The reaction according to the invention is carried out in the presence of at least one, in particular one, base.

The base is preferably chosen from the group consisting of alkali metal salts, alkoxides, the excess amines described above and tertiary amines.

Examples of suitable alkali metal salts are sodium phosphate, potassium phosphate, sodium carbonate, potassium carbonate, sodium acetate and potassium acetate. They are preferably used in anhydrous form in the preparation of the carboxylic acid esters and carboxamides according to the process according to the invention. Use is made in particular of anhydrous potassium carbonate.

Examples of suitable alkoxides are the sodium and potassium alkoxides of the alcohols described above, in particular sodium and potassium methoxide, ethoxide, isopropoxide, tert-butoxide and phenoxide.

Examples of suitable tertiary amines are trimethylamine, triethylamine, diisopropylethylamine, N-methylpiperidine, pyridine, collidine, lutidine, 4-dimethylaminopyridine, 1,4-diazabicyclo[2.2.2]octane (DABCO), 1,5-diazabicyclo[4.3.0]non-5-ene (DBN) and 1,8-diazabicyclo[5.4.0]undec-7-ene (DBU), in particular triethylamine and DBU.

In the reaction according to the process according to the invention, the aromatic or heteroaromatic halides of the general formula I are reacted with water, alcohols or amines preferably in a molar ratio of halide I:water, alcohol or amine of 0.5:1 to 2:1, in particular of 0.8:1 to 1.2:1, in each case based on the respective nucleophilic oxygen atom or nitrogen atom.

In this connection, the zero-valent or divalent palladium compound is preferably used in an amount of 0.001 to 5 mol %, in particular of 0.01 to 1 mol %, in each case based on the halide I.

The bidentate diphosphane II is particularly preferably used in a molar ratio of bidentate diphosphane II to palladium compound of 0.01:1 to 10 000:1, in particular 0.1:1 to 100:1.

The base is preferably used in an equivalent ratio of halogen atom in the halide I to base=1:1 to 1:4. When an alkali metal salt is employed, an equivalent ratio of 1:1 to 1:4, in particular of 1:2, is used in particular. When a tertiary amine is employed, an equivalent ratio of 1:0.1 to 1:4, in particular of 1:0.2 to 1:2, is particularly preferably used.

The reaction according to the process according to the invention can be carried out in the absence of an organic solvent. However, it can also be carried out in an aromatic solvent or a polar aprotic organic solvent.

The aromatic solvents are preferably chosen from the group consisting of excess aromatic or heteroaromatic halides of the general formula I, toluene and the xylenes.

The polar aprotic organic solvents are preferably chosen from the group consisting of amides, ethers, sulfones and nitriles. Use is preferably made of dimethylformamide, dimethylacetamide, N-methylpyrrolidone, hexamethylphosphoramide, 1,4-dioxane, sulfolane, acetonitrile, propionitrile and mixtures thereof.

The organic solvent is particularly preferably, in the reaction of the halides I with alcohols or amines, essentially or completely anhydrous. This means that it exhibits a water content of <1000 ppm, in particular <100 ppm.

The reaction according to the invention can furthermore be carried out in the presence of an organic monophosphane. The monophosphanes comprise at least one alkyl radical, cycloalkyl radical or aryl radical. The monophosphanes preferably comprise two and in particular three radicals chosen from the group consisting of alkyl radicals, cycloalkyl radicals or aryl radicals. These radicals can also be cyclically linked to one another. Use is made in particular of triphenylphosphane.

The palladium complexes of the diphosphanes II described above are preferably used in combination with at least one, in particular one, monophosphane.

The reaction according to the process according to the invention is preferably carried out at a temperature of between 90 and 200° C., preferably from 100 to 180° C. and in particular from 110 to 150° C.

The reaction according to the process according to the invention can be carried out under slight negative pressure, standard pressure or excess pressure. The pressure applied is in this connection determined in particular by the carbon monoxide partial pressure. The reaction is preferably carried out at a carbon monoxide partial pressure of 0.9 to 100 bar (90 to 10 000 kPa), particularly preferably of 1 to 50 bar (100 to 5000 kPa), in particular of 5 to 20 bar (500 to 2000 kPa).

The reaction mixtures obtained according to the process according to the invention are preferably worked up under aqueous conditions. In this connection, the reaction mixtures are brought into contact with water or aqueous solution. After the acidification of the aqueous reaction mixtures, the carboxylic acids, carboxylic acid esters and carboxamides prepared in the procedure according to the invention can be isolated by extraction with organic solvents and subsequent removal of the organic solvents. If appropriate, it may be advantageous, in particular if water-miscible solvents have been used in the reaction according to the process according to the invention, to at least partially remove the solvents before the extraction, for example by distillation.

The process according to the invention and the workup of the reaction mixtures obtained present no unusual features with regard to the method but can be carried out with the help of the standard and known processes and devices of organic chemistry.

EXAMPLES AND COMPARATIVE EXPERIMENTS

Preparation Example

Preparation of Pd[2,2-dimethyl-1,3-bis(diphenylphosphanyl)propane]$_2$Cl$_2$, Pd(Pepstar)$_2$Cl$_2$ Pd(Pepstar)$_2$Cl$_2$ was prepared analogously to M. R. Mason and J. G. Verkade, Organometallics, 1992, 11, 2212-2220.

Pd(PhCN)$_2$Cl$_2$ (0.31 mmol) was placed in a Schlenk flask. A total of 50 ml of toluene was successively added for dissolution. Pepstar (0.33 mmol) was dissolved in 5 ml of toluene and added to the orange-colored Pd solution. In the course of this, a pale-yellow solid precipitated while the solution lost its color.

After stirring for a further 1 h, the solid was filtered off and washed three times with each time 3 ml of hexane. The complex was dried under vacuum to constant weight. PdCl2(Pepstar)$_2$ was obtained in a quantitative yield (191.5 mg).

Examples 1 to 5-4

Carboxymethylation of chloroacetophenone to give methyl 4-acetylbenzoate

Reaction Equation:

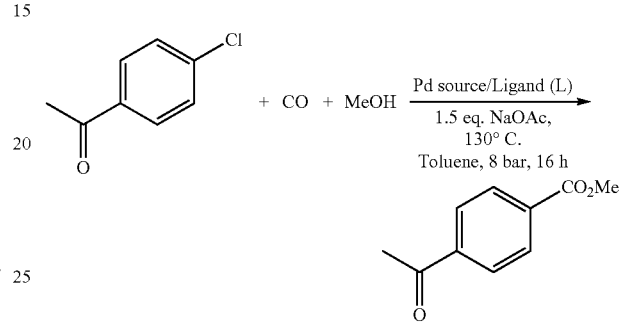

Example 1

Methoxycarbonylation with 2,2-dimethyl-1,3-bis(diphenylphosphanyl)propane (Pepstar) as ligand (Method A)

The catalyst Pd(OAc)$_2$ (Ac=acetyl; 0.3 mol %) and the ligand 2,2-dimethyl-1,3-bis(diphenylphosphino)propane (Pepstar; 1.1 mol %) were weighed out in a glovebox under a protective gas and dissolved in 5 ml of degassed methanol. Subsequently, 20 ml of degassed toluene, the substrate 4-acetylchlorobenzene (10 mmol) and sodium acetate (15 mmol) were added to the charge.

The reaction charge was transferred into an autoclave purged with argon and the autoclave was purged three times with carbon monoxide. Subsequently, the reaction solution was heated to 130° C. Subsequently, a CO pressure of 6 bar was applied. The reaction was run at 8 bar and 130° C. for 16 h. The autoclave was cooled down and opened. The gas chromatography analysis revealed, after 16 h, a quantitative conversion with a selectivity of 85%.

Analysis:
DB-1, 5 min 60° C.; 10°/min to 260° C.

| Retention time [min] | Compound |
|---|---|
| 14.67 | 4-chloroacetophenone |
| 18.28 | Product |

Example 2

Methoxycarbonylation with 2,2-dimethyl-1,3-bis(diphenylphosphanyl)propane (Pepstar) as ligand (modified Method A)

The catalyst Pd(OAc)$_2$ (0.1 mol %) and the ligand 2,2-dimethyl-1,3-bis(diphenylphosphino)propane (Pepstar, 1.1 mol %) were weighed out in a glovebox under a protective gas and dissolved in 5 ml of degassed methanol. Subsequently, 20 ml of degassed toluene, the substrate 4-acetylchlorobenzene (10 mmol) and sodium acetate (15 mmol) were added to the charge.

The reaction charge was transferred into an autoclave purged with argon and the autoclave was purged three times with carbon monoxide. Subsequently, the reaction solution was heated to 130° C. Subsequently, a CO pressure of 6 bar was applied. The reaction was run at 8 bar and 130° C. for 16 h. The autoclave was cooled down and opened. The gas chromatography analysis revealed, after 16 h, a conversion of 99% with a selectivity of 82%.

Example 3

Methoxycarbonylation with Pd(Pepstar)$_2$Cl$_2$ (Method B)

The catalyst Pd(Pepstar)$_2$Cl$_2$ (0.1 mol %; cf. the preparation example) and the ligand 2,2-dimethyl-1,3-bis(diphenylphosphino)propane (Pepstar, 0.3 mol %) were weighed out in a glovebox under a protective gas and dissolved in 5 ml of degassed methanol. Subsequently, 20 ml of degassed toluene, the substrate 4-acetylchlorobenzene (10 mmol) and NaOAc (15 mmol) were added to the charge.

The reaction charge was transferred into an autoclave purged with argon and the autoclave was purged three times with carbon monoxide. Subsequently, the reaction solution was heated to 130° C. Subsequently, a CO pressure of 6 bar was applied. The reaction was run at 8 bar and 130° C. for 24 h. The autoclave was cooled down and opened. The gas chromatography analysis revealed, after 24 h, a conversion of 99% with a selectivity of 82.6%.

Example 4

Methoxycarbonylation with Pd(Pepstar)$_2$Cl$_2$ (Method C)

The catalyst Pd(Pepstar)$_2$Cl$_2$ (0.1 mol %) was weighed out in a glovebox under a protective gas and dissolved in 5 ml of degassed methanol. Subsequently, 20 ml of degassed toluene, the substrate 4-acetylchlorobenzene (10 mmol) and NaOAc (15 mmol) were added to the charge.

The reaction charge was transferred into an autoclave purged with argon and the autoclave was purged three times with carbon monoxide. Subsequently, the reaction solution was heated to 130° C. Subsequently, a CO pressure of 6 bar was applied. The reaction was run at 8 bar and 130° C. for 16 h. The autoclave was cooled down and opened. The gas chromatography analysis revealed, after 16 h, a conversion of 85% with a selectivity of 81.7%.

Examples 5-1 to 5-4

Methoxycarbonylation with Pd(Pepstar)$_2$Cl$_2$ and triphenylphosphane (Method D)

General Experimental Method:
The catalyst Pd(Pepstar)$_2$Cl$_2$ (0.1 mol %) and the ligand triphenylphosphane were weighed out in a glovebox under a protective gas and dissolved in 5 ml of degassed methanol. Subsequently, 20 ml of degassed toluene, the substrate 4-acetylchlorobenzene (10 mmol) and NaOAc (15 mmol) were added to the charge.

The reaction charge was transferred into an autoclave purged with argon and the autoclave was purged three times with carbon monoxide. Subsequently, the reaction solution was heated to 130° C. Subsequently, a CO pressure of 6 bar was applied. The reaction was run at 8 bar and 130° C. for 16 h. The autoclave was cooled down and opened. The conversions and selectivities after 16 h or 24 h were determined with the help of gas chromatography. A summary of the molar ratios of Pd(Pepstar)$_2$C$_2$:triphenylphosphine, the conversions and the selectivities is given in the following table No. 1.

TABLE NO. 1

| No. 5- | Pd(Pepstar)$_2$Cl$_2$:triphenylphosphine | Conversion [%] | Selectivity [%] |
|---|---|---|---|
| 1 | 1:3 | 74.5 | 80.2 |
| 2* | 1:5 | 92.4 | 83.7 |
| 3* | 1:7.5 | 84.0 | 100.0 |
| 4* | 1:10 | 82.3 | 100.0 |

*The reaction time in these experiments was 24 h.

Examples 6-1 to 6-3 and 7

Amidocarbonylation of chloracetophenone with aniline to give 4-acetyl-N-phenylbenzamide Reaction Equation

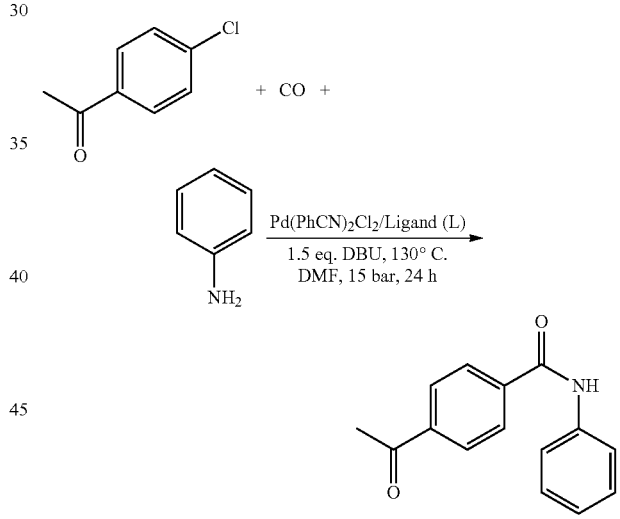

Example 6-1

Amidocarbonylation with 2,2-dimethyl-1,3-bis(diphenylphosphanyl)propane (Pepstar) as ligand
General Experimental Method:
The catalyst Pd(PhCN)$_2$Cl$_2$ (0.5 mol %) and the ligand 2,2-dimethyl-1,3-bis(diphenyl-phosphanyl)propane (Pepstar, 1.5 mol %) were weighed out in a glovebox under a protective gas and dissolved in 5 ml of degassed DMF. Subsequently, 20 ml of degassed DMF, the substrate 4-acetylchlorobenzene (10 mmol), aniline (15 mmol) and base (15 mmol) were added to the charge.

The reaction charge was transferred into an autoclave purged with argon and the autoclave was purged three times with carbon monoxide. Subsequently, the reaction solution was heated to 130° C. Subsequently, a CO pressure of 15 bar was applied. The reaction was run at 15 bar and 130° C. or 150° C. for 24 h. The autoclave was cooled down and opened. A gas chromatography analysis of the reaction output was carried out according to the following table No. 2.

Analysis:
DB-1, 5 min 60° C.; 10°/min to 260° C.

TABLE NO. 2

| Reaction time [min] | Compound |
|---|---|
| 9.40 | Aniline |
| 14.72 | 4-Chloroacetophenone |
| 29.54 | Product |

The conversions and selectivities obtained in Examples 6-1 to 6-3 with different bases are shown in the following table No. 3.

TABLE NO. 3

| No. 6- | Bases | Conversion [%] | Selectivity [%] |
|---|---|---|---|
| 1 | DBU[a] | 99.1 | 70.1 |
| 2* | NEt₃[b] | 89.1 | 29.4 |
| 3* | K₂CO₃ | 96.7 | 78.0 |

*The reaction temperature in these experiments was 150° C.
[a]1,8-Diazabicyclo[5.4.0]undec-7-ene
[b]Triethylamine

Example 7

Amidocarbonylation with 2-butyl-2-ethyl-1,3-bis(diphenylphosphanyl)propane (Bustar) as ligand The catalyst Pd(PhCN)$_2$Cl$_2$ (0.5 mol %) and the ligand 2-butyl-2-ethyl-1,3-bis(diphenylphosphanyl)propane (Bustar; 1.5 mol %) were weighed out in a glovebox under a protective gas and dissolved in 5 ml of degassed DMF. Subsequently, 20 ml of degassed DMF, the substrate 4-acetylchlorobenzene (10 mmol), aniline (15 mmol) and DBU (15 mmol) were added to the charge.

The reaction charge was transferred into an autoclave purged with argon and the autoclave was purged three times with carbon monoxide. Subsequently, the reaction solution was heated to 130° C. Subsequently, a CO pressure of 15 bar was applied. The reaction was run at 15 bar and 130° C. for 16 h. The autoclave was cooled down and opened. The gas chromatography analysis revealed, after 24 h, a conversion of 97.7% and a selectivity of 91.4%.

Examples 8 and 9 and Comparative Experiments C1 and C2

Carboxylation of 4-bromotoluene to give 4-methylbenzoic acid

Reaction Equation:

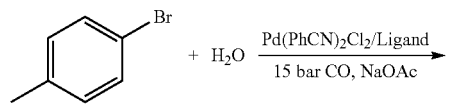
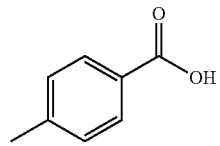

General Experimental Method:

NaOAc (4.1 mmol) was placed in a reactor unit consisting of four parallel reactors. Pd(OAc)$_2$ (0.028 mmol, 1 mol %) and the corresponding ligand (0.084 mmol, 3 mol %) were added in DMF (10 ml). The resulting reaction mixture was agitated at ambient temperature for 30 min. Subsequently, 4-bromotoluene (2.8 mmol) and water (1 ml) were metered in. After 10 min at 15 bar CO and room temperature, the reaction mixture was heated to 140° C. After 16 h, the reactors were cooled down and reduced in pressure. The reactor output was analyzed by means of gas chromatography (cf. table No. 4).

Analysis:
DB-1, 5 min. 60° C.; 10°/min to 260° C.

TABLE NO. 4

| Retention time [min] | Compound |
|---|---|
| 11.22 | 4-Bromotoluene |
| 15.51 | 4-Methylbenzoic acid |

The quantitative ratios used and the conversions and selectivities obtained after 16 h in examples 8 and 9 and comparative experiments C1 and C2 are represented in the following table No. 5.

TABLE NO. 5

| Ligand | Example 8 Reactor 1 Pepstar | Example 9 Reactor 2 Bustar | Comparison C1 Reactor 3 DPPP[a] | Comparison C2 Reactor 4 DPPF[b] |
|---|---|---|---|---|
| Starting material [%] | 0.39 | 0.50 | 0.58 | 0.93 |
| Product [%] | 5.91 | 6.07 | 3.12 | 2.21 |
| Conversion [%] | 97.2 | 96.3 | 94.9 | 88.4 |
| Selectivity [%] | 44.2 | 47.1 | 28.7 | 31.2 |

[a]1,3-Bis(diphenylphosphanyl)propane
[b]1,1'-Bis(diphenylphosphanyl)ferrocene

The comparison of the conversions and the selectivities corroborated for the Pepstar and Bustar were clearly superior to the other ligands.

We claim:

1. A process for preparing an aromatic or a heteroaromatic carboxylic acid, carboxylic acid ester or carboxamide by reacting an aromatic or a heteroaromatic halide of the general formula I:

$$R(-X)_n \qquad (I),$$

with carbon monoxide and water, ammonia, an alcohol or an amine in the presence of a base and a zero-valent or a divalent palladium compound and a bidentate diphosphane or a complex of zero- or divalent palladium with a bidentate diphosphane,
wherein:
n is an integer from 1 to 6,
R is a substituted or unsubstituted aromatic or heteroaromatic radical and
X is chlorine, bromine or iodine atom; and wherein the bidentate diphosphane has the general formula II:

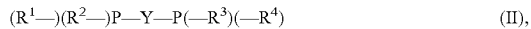

$(R^1—)(R^2—)P—Y—P(—R^3)(—R^4)$ (II), wherein
R$^1$ to R$^4$ are independently of one another, identically or differently, unsubstituted aryl radical or aryl radical substituted with at least one radical exhibiting a positive resonance effect or a positive inductive effect, an unsubstituted or a substituted cyclopentyl or cyclohexyl; and
Y is a hydrocarbon group with a total of 2 to 20 carbon atoms, wherein at least one of the carbon atoms carries only one or no hydrogen atom as substituent;
provided the reaction between 4-bromo-3-difluoromethyl-1-methylpyrazole with 2-(3,4,5-trifluorophenyl)aniline and carbon monoxide
(a) in N-methylpyrrolidone in the presence of Pd(C$_6$H$_5$CN)$_2$Cl$_2$, 2,2-dimethyl-1,3-bis(diphenylphosphanyl)propane and potassium carbonate; or
(b) in acetonitrile in the presence of Pd(C$_6$H$_5$CN)$_2$Cl$_2$, 3,3-bis(diphenylphosphanylmethylene)heptane, triethylamine and potassium carbonate;
to give N-[2-(3,4,5-trifluorophenyl)phenyl]-3-difluoromethyl-1-methylpyrazole-4-carboxamide is excluded.

2. The process of claim 1, wherein the radicals R$^1$ to R$^4$ are selected from the group consisting of an unsubstituted aryl radical with from 6 to 20 carbon atoms in the ring or in the rings, a substituted aryl radical with from 6 to 20 carbon atoms which are substituted with at least one radical exhibiting a positive resonance effect or a positive inductive effect, and an unsubstituted or a substituted cyclopentyl or cyclohexyl radicals.

3. The process of claim 1, wherein, in the general formula II, the radicals R$^1$ to R$^4$ are identical.

4. The process of claim 1, wherein the radical exhibiting a positive resonance effect or a positive inductive effect is a branched or unbranched alkyl radical with one carbon atom or from 2 to 12 carbon atoms.

5. The process according of claim 1, wherein the radicals R$^1$ to R$^4$ are unsubstituted phenyl or cyclohexyl radicals.

6. The process of claim 1, wherein the hydrocarbon group Y comprises a total of from 3 to 15 carbon atoms.

7. The process of claim 1, wherein the hydrocarbon group Y consists exclusively of hydrocarbon atoms and hydrogen atoms.

8. The process of claim 1, wherein the hydrocarbon group Y has the general formula III:

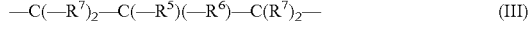

$—C(—R^7)_2—C(—R^5)(—R^6)—C(R^7)_2—$ (III)

wherein the radicals R$^5$ and R$^6$ are selected from the group consisting of
hydrogen;
linear or branched alkyl radicals with one carbon atom or from 2 to 12 carbon atoms;
substituted and unsubstituted cycloalkyl radicals with from 5 to 16 carbon atoms in the ring or in the rings;
substituted and unsubstituted aryl radicals with from 6 to 20 carbon atoms in the ring or in the rings;
substituted and unsubstituted x-cycloalkylalkan-1-yl radicals with from 5 to 16 carbon atoms in the cycloalkyl radical or substituted and unsubstituted x-arylalkan-1-yl radicals with from 6 to 20 carbon atoms in the aryl radical and also in each case one carbon atom or from 2 to 6 carbon atoms in the 1,x-alkylene radical, in which x=integer from 1 to 6; and
substituted and unsubstituted y-arylcycloalkan-1-yl radicals with from 6 to 20 carbon atoms in the aryl radical and from 5 to 16 carbon atoms in the 1,y-cycloalkylene radical, in which y=integer from 1 to 12; and
wherein radicals R$^7$ are selected from the group consisting of hydrogen atom, fluorine atom, chlorine atom, bromine atom, nitrile group, nitro group and radicals R$^5$ and R$^6$.

9. The process of claim 8, wherein x=integer from 1 to 4; or y=integer from 1 to 4.

10. The process of claim 8, wherein, in the general formula III, neither of the radicals R$^5$ and R$^6$ is a hydrogen atom.

11. The process of claim 8, wherein, in the general formula III, the radicals R$^5$ and R$^6$ are identical.

12. The process of claim 10, wherein the radicals R$^5$ and R$^6$ are linked cyclically to one another.

13. The process of claim 8, wherein the radicals R$^5$ and R$^6$ are selected from the group consisting of methyl, ethyl, propyl, n-butyl, n-pentyl, n-hexyl, phenyl, benzyl, cyclopentyl and cyclohexyl.

14. The process of claim 8, wherein the radicals R$^7$ are hydrogen atoms.

15. The process of claim 13, wherein the bidentate diphosphanes of the general formula II are chosen from the group consisting of
2-methyl-, 2-ethyl-, 2-propyl-, 2-(n-butyl)-, 2-(n-pentyl)-, 2-(n-hexyl)-, 2-cyclohexyl- and 2-phenyl-1,3-bis(diphenylphosphanyl)propane or 1,3-bis(dicyclohexylphosphanyl)propane,
2,2-dimethyl-, 2,2-diethyl-, 2,2-dipropyl-, 2,2-di(n-butyl)-, 2,2-di(n-pentyl)-, 2,2-dicyclohexyl- or 2,2-diphenyl-1,3-bis(diphenylphosphanyl)propane or 1,3-bis(dicyclohexylphosphanyl)propane,
2-methyl-2-ethyl-, -2-propyl-, -2-(n-butyl)-, -2-(n-pentyl)-, -2-(n-hexyl)-, 2-cyclohexyl- and -2-phenyl-1,3-bis(diphenylphosphanyl)propane or 1,3-bis(dicyclohexylphosphanyl)propane,
2-ethyl-2-propyl-, -2-(n-butyl)-, -2-(n-pentyl)-, -2-(n-hexyl)-, 2-cyclohexyl- and 2-phenyl-1,3-bis(diphenylphosphanyl)propane or 1,3-bis(dicyclohexylphosphanyl)propane,
2-propyl-2-(n-butyl)-, -2-(n-pentyl)-, -2-(n-hexyl)-, -2-cyclohexyl- and 2-phenyl-1,3-bis(diphenylphosphanyl)propane or 1,3-bis(dicyclohexylphosphanyl)propane,
2-(n-butyl)-2-(n-pentyl)-, -2-(n-hexyl)-, -2-cyclohexyl- and -2-phenyl-1,3-bis(diphenylphosphanyl)propane or 1,3-bis(dicyclohexylphosphanyl)propane,
2-(n-pentyl)-2-(n-hexyl)-, -2-cyclohexyl- and -2-phenyl-1,3-bis(diphenylphosphanyl)propane and -1,3-bis(dicyclohexylphosphanyl)propane,
2-(n-hexyl)-2-cyclohexyl- or 2-phenyl-1,3-bis(diphenylphosphanyl)propane and -1,3-bis(dicyclohexylphosphanyl)propane, and
2-cyclohexyl-2-phenyl-1,3-bis(diphenylphosphanyl)propane or 1,3-bis(dicyclohexylphosphanyl)propane.

16. The process of claim 15, wherein the bidentate diphosphanes of the general formula II are chosen from the group consisting of 2-ethyl-2-butyl- and 2,2-dimethyl-1,3-bis(diphenylphosphanyl)propane.

17. The process of claim 1, wherein the aromatic radical R of the general formula I is derived from benzene or a polycyclic aromatic hydrocarbon and the heteroaromatic radical R is derived from a monocyclic or polycyclic aromatic heterocycle.

18. The process of claim 17, wherein the polycyclic aromatic hydrocarbon is selected from the group consisting of
hydrocarbons, in which at least two benzene nuclei, at least two fused polycyclic aromatic hydrocarbons or at least one benzene nucleus and at least one fused polycyclic aromatic hydrocarbon are linked to one another via at least one carbon-carbon single bond, and fused polycyclic aromatic hydrocarbons.

19. The process of claim 17, wherein the aromatic heterocycle comprises at least one heteroatom selected from the group consisting of nitrogen atom, oxygen atom and sulfur atom.

20. The process of claim 1, wherein the alcohol is selected from the group consisting of aliphatic, cycloaliphatic, aromatic and heteroaromatic alcohols with from 1 to 4 hydroxyl groups in the molecule.

21. The process of claim 1, wherein the amine is selected from the group consisting of aliphatic, cycloaliphatic, cyclic, aromatic and heteroaromatic primary and secondary amines with from 1 to 4 amino groups in the molecule.

22. The process of claim 20, wherein the respective parent substance of the alcohols and/or of the amines is substituted with at least one inert substituent.

23. The process of claim 1, wherein the zero-valent palladium compound is chosen from the group consisting of metallic palladium and organopalladium(0) compounds and the divalent palladium compound is chosen from the group consisting of organopalladium(II) compounds and palladium (II) salts.

24. The process of claim 23, wherein the metallic palladium is supported.

25. The process of claim 23, wherein the organopalladium (0) compound is chosen from the group consisting of tris($\eta^2$-alkene)palladium(0), bis(carbene)-palladium(0), palladium (0)-phosphane complexes and mixed palladium(0)-($\eta^2$-alkene)-phosphane complexes, the organopalladium(II) compound is chosen from the group consisting of palladium (II)-chelate complexes, donor adducts with monovalent ligands and $\pi$-bonded ligands and complexes with monovalent ligands and halides, and the palladium(II) salts is chosen from the group consisting of palladium(II) halides and carboxylates.

26. The process of claim 1, wherein the base is chosen from the group consisting of alkali metal salts, alkoxides, excess amines, as defined in claim 22, and tertiary amines.

27. The process of claim 1, wherein the aromatic or heteroaromatic halide of the general formula I is reacted with water, alcohol or amine in a molar ratio of halide I:water, alcohol or amine of 0.5:1 to 2:1, based on the respective nucleophilic oxygen atom or nitrogen atom.

28. The process of claim 1, wherein the zero-valent or divalent palladium compound is used in an amount of 0.001 to 5 mol %, based on the halide I.

29. The process of claim 1, wherein the base is used in an equivalent ratio of halogen atom in the halide I to base=1:1 to 1:4.

30. The process of claim 1, wherein the reaction is carried out in an aromatic solvent or a polar aprotic organic solvent.

31. The process of claim 30, wherein the organic solvent is selected from the group consisting of an excess aromatic or heteroaromatic halide of the general formula I, toluene, a xylene, an amide, an ether, a sulfone and a nitrile.

32. The process of claim 31, wherein the organic solvent in the reaction of the halide I with the alcohol or amine is essentially or completely anhydrous.

33. The process of claim 1, wherein use is also made, in addition to the diphosphanes of the general formula II or their complexes with zero-valent or divalent palladium, of at least one organic monophosphane.

34. The process of claim 1, wherein the reaction is carried out at a temperature between 90 and 200° C.

35. The process of claim 1, wherein the reaction is carried out at a carbon monoxide partial pressure of 0.9 to 100 bar (90 to 10 000 kPa).

* * * * *

UNITED STATES PATENT AND TRADEMARK OFFICE
CERTIFICATE OF CORRECTION

PATENT NO. : 8,703,992 B2
APPLICATION NO. : 12/994271
DATED : April 22, 2014
INVENTOR(S) : Nina Challand et al.

It is certified that error appears in the above-identified patent and that said Letters Patent is hereby corrected as shown below:

In the Claims

In claim 15, col. 22, line 30, after "2,2-di(n-pentyl)-," insert -- 2,2-di(n-hexyl)- --.

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

PATENT NO.        : 8,703,992 B2                    Page 1 of 1
APPLICATION NO.  : 12/994271
DATED             : April 22, 2014
INVENTOR(S)       : Challand et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 457 days.

Signed and Sealed this
Twenty-ninth Day of September, 2015

Michelle K. Lee
*Director of the United States Patent and Trademark Office*